(12) United States Patent
Erden et al.

(10) Patent No.: US 7,754,165 B2
(45) Date of Patent: **\*Jul. 13, 2010**

(54) HIGH PRESSURE PARALLEL REACTOR

(75) Inventors: Lynn Van Erden, Livermore, CA (US);
Howard Turner, Campbell, CA (US);
David M. Lowe, Mountain View, CA (US)

(73) Assignee: Symyx Solutions, Inc., Sunnyvale, CA (US)

( * ) Notice: Subject to any disclaimer, the term of this patent is extended or adjusted under 35 U.S.C. 154(b) by 170 days.

This patent is subject to a terminal disclaimer.

(21) Appl. No.: 11/708,301

(22) Filed: Feb. 20, 2007

(65) Prior Publication Data

US 2007/0154361 A1 Jul. 5, 2007

Related U.S. Application Data

(60) Continuation of application No. 11/363,026, filed on Feb. 27, 2006, which is a division of application No. 09/619,416, filed on Jul. 19, 2000, now Pat. No. 7,018,589.

(51) Int. Cl.
*B01J 3/00* (2006.01)
*B01J 19/00* (2006.01)

(52) U.S. Cl. .................. 422/242; 422/196; 422/130; 422/129

(58) Field of Classification Search .............. 422/196, 422/130, 242, 129
See application file for complete search history.

(56) References Cited

U.S. PATENT DOCUMENTS

| 3,617,033 | A | 11/1971 | Ichikawa et al. |
| 3,881,872 | A | 5/1975 | Naono |
| 4,000,492 | A | 12/1976 | Willens |
| 4,180,943 | A | 1/1980 | Smith et al. |
| 4,493,815 | A | 1/1985 | Fernwood et al. |
| 4,787,988 | A | 11/1988 | Bertoncini et al. |
| 4,895,706 | A | 1/1990 | Root et al. |
| 4,927,604 | A | 5/1990 | Mathus et al. |
| 4,990,076 | A | 2/1991 | Lynch et al. |

(Continued)

FOREIGN PATENT DOCUMENTS

DE 198 09 477 A1 9/1999

(Continued)

OTHER PUBLICATIONS

Diploma Thesis Christian Hoffman, Frankfurt, Germany, Aug. 1998 (Partial English Translation attached).

(Continued)

*Primary Examiner*—Walter D Griffin
*Assistant Examiner*—Natasha Young
(74) *Attorney, Agent, or Firm*—Cindy Kaplan

(57) ABSTRACT

An apparatus for use in parallel reaction of materials. The apparatus includes a base having a plurality of reaction wells, each of the reaction wells having a closed lower end and open upper end for receiving reactant materials. A cover is configured for sealing engagement with the base to form a housing enclosing the plurality of reaction wells and defining a common pressure chamber in communication with the reaction wells. The apparatus further includes an inlet port in communication with the pressure chamber for supplying pressurized fluid to the chamber to pressurize the reaction wells. The housing is configured to sustain a pressure substantially above atmospheric pressure.

19 Claims, 11 Drawing Sheets

U.S. PATENT DOCUMENTS

| | | | |
|---|---|---|---|
| 5,011,779 A | 4/1991 | Maimon | |
| 5,035,866 A | 7/1991 | Wannlund | |
| 5,183,564 A | 2/1993 | Hong | |
| 5,190,666 A | 3/1993 | Bisconte | |
| 5,190,734 A | 3/1993 | Frushour | |
| 5,205,845 A | 4/1993 | Sacks et al. | |
| 5,246,665 A | 9/1993 | Tyranski et al. | |
| 5,324,483 A | 6/1994 | Cody et al. | |
| 5,428,118 A | 6/1995 | Painter et al. | |
| 5,443,791 A | 8/1995 | Cathcart et al. | |
| 5,516,490 A | 5/1996 | Sanadi | |
| 5,529,756 A | 6/1996 | Brennan | |
| 5,544,683 A | 8/1996 | Guhl | |
| 5,593,642 A | 1/1997 | DeWitt et al. | |
| 5,624,815 A | 4/1997 | Grant et al. | |
| 5,714,127 A * | 2/1998 | DeWitt et al. | 422/131 |
| 5,716,584 A | 2/1998 | Baker et al. | |
| 5,746,982 A | 5/1998 | Saneii et al. | |
| 5,766,556 A | 6/1998 | DeWitt et al. | |
| 5,792,430 A | 8/1998 | Hamper | |
| 5,846,396 A | 12/1998 | Zanzucchi et al. | |
| 5,897,842 A | 4/1999 | Dunn et al. | |
| 6,027,694 A | 2/2000 | Boulton et al. | |
| 6,042,789 A | 3/2000 | Antonenko et al. | |
| 6,045,755 A | 4/2000 | Lebl et al. | |
| 6,063,633 A | 5/2000 | Willson, III | |
| 6,106,783 A | 8/2000 | Gamble | |
| 6,117,397 A * | 9/2000 | Antonenko et al. | 506/40 |
| 6,132,686 A | 10/2000 | Gallup et al. | |
| 6,171,555 B1 | 1/2001 | Cargill et al. | |
| 6,190,619 B1 | 2/2001 | Kilcoin et al. | |
| 6,238,627 B1 * | 5/2001 | McGowan et al. | 422/130 |
| 6,250,707 B1 | 6/2001 | Dintner et al. | |
| 6,264,891 B1 | 7/2001 | Heyneker et al. | |
| 6,306,658 B1 * | 10/2001 | Turner et al. | 436/37 |
| 6,309,608 B1 | 10/2001 | Zhou et al. | |
| 6,376,256 B1 | 4/2002 | Dunnington et al. | |
| 6,410,332 B1 | 6/2002 | Desrosiers et al. | |
| 6,455,316 B1 * | 9/2002 | Turner et al. | 436/37 |
| 6,485,692 B1 | 11/2002 | Freitag et al. | |
| 6,537,500 B1 | 3/2003 | Brenner et al. | |
| 6,572,828 B1 | 6/2003 | Potyrailo et al. | |
| 6,770,482 B1 | 8/2004 | Flanagan et al. | |
| 6,890,492 B1 * | 5/2005 | Turner et al. | 506/33 |
| 6,994,827 B2 * | 2/2006 | Safir et al. | 422/100 |
| 7,018,589 B1 * | 3/2006 | Erden et al. | 422/130 |
| 7,141,218 B2 * | 11/2006 | Van Erden et al. | 422/130 |
| 7,172,732 B2 * | 2/2007 | Van Erden et al. | 422/130 |

FOREIGN PATENT DOCUMENTS

| | | |
|---|---|---|
| WO | WO 97/32208 | 9/1997 |
| WO | WO 97/45443 | 12/1997 |
| WO | WO 98/15813 | 4/1998 |
| WO | WO 98/36826 | 8/1998 |
| WO | WO 00/03805 | 1/2000 |
| WO | WO 01/14529 | 3/2000 |
| WO | WO 01/00315 | 1/2001 |
| WO | WO 01/05497 | 1/2001 |

OTHER PUBLICATIONS

Poster Presentation, Hofffman et al., Frankfurt, Germany, Sep. 25, 1998 (Partial English Translation attached).

Grunwald et al., "Investigation of Coolant Mixing in Pressurized Water Reactors at the Rossendorf Mixing Test Facility Rocom".

Heiszwolf, Johan J. "runaway in Stirred Tanks", http://www.dct.tudelft.nl/monoliet/heiszwolf/runaway.html.

http://www.louisville.edu/speed/Mixing_Lab.htm.

http://www.epa.gov/ORD/NRMRL/Pubs/2001/water/600r01021c2/pdf/.

http://www.onlineconversion.com/.

Product Brochure for Radleys Titan Specialist Micro Titer Plates, 8 pages.

Christian Hoffmann, Anne Wolf and Ferdi Schuth, "Parallel Synthesis and Testing of Catalysts under Nearly Conventional Testion Conditions", Angew. Chem. Int. 1999, 38, No. 18.

Product Brochure "Calypso System Valve Base Reaction Frame", Charybdis Technologies, Inc.

* cited by examiner

HIGH PRESSURE PARALLEL REACTOR

RELATED APPLICATION

This patent application is a continuation of U.S. patent application Ser. No. 11/363,026, filed Feb. 27, 2006, which is a divisional of U.S. patent application Ser. No. 09/619,416, filed Jul. 19, 2000, which are both incorporated herein by reference in their entirety.

FIELD OF THE INVENTION

The present invention relates generally to parallel batch reactors, and more particularly, to high pressure reactors for parallel synthesis and screening of materials.

BACKGROUND OF THE INVENTION

The discovery of new materials with novel chemical and physical properties often leads to the development of new and useful technologies. The discovery of new materials depends largely on the ability to synthesize and analyze new compounds. Scientists are thus, always searching for a more efficient, economical, and systematic approach for the synthesis of novel materials. Combinatorial technologies are often used to accelerate the speed of research, maximize the opportunity for breakthroughs, and expand the amount of available information. Combinatorial chemistry involves synthesizing microscale quantities of a compound and then testing thousands of compounds quickly.

The use of combinatorial technologies allows high density libraries of very large numbers of materials to be created using parallel synthesis. High throughput screens are then used to test these materials for desired properties to identify potential optimized compounds. Combinatorial technologies may be used to optimize and validate many variations of a material, formulation, or microdevice. Variables such as temperature, pressure, atmosphere, and concentration can be quickly adjusted and tested in a single experiment.

In parallel synthesis, different compounds are synthesized in separate vessels, often in an automated fashion. A commonly used format for parallel synthesis is a multi-well microtiter plate. Robotic instrumentation can be used to add different reagents or catalysts to individual wells of a microtiter plate in a predefined manner to produce combinatorial libraries. Devices have been developed for automating combinatorial parallel synthesis. One such device includes reaction blocks containing multiple reaction vessels each individually sealed. These devices often require substantial sealing arrangements and do not provide means for pressurizing the individual vessels. Other devices supply an inert gas to a plurality of reactor vessels, however, the gas is only supplied at one or two psi above atmospheric pressure to control the environment during the reaction. These devices are not designed to withstand high pressure operation.

SUMMARY OF THE INVENTION

An apparatus and method for synthesis and screening of materials are disclosed.

A method for reacting a plurality of materials in parallel with a reactor vessel having a plurality of reaction wells formed in a base of the vessel, each of the reaction wells having an open end exposed to a common pressure chamber defined by the reactor vessel, generally comprises: opening a cover of the reactor vessel; inserting components into the reaction wells; closing the cover of the reactor vessel to create a sealed chamber; and supplying a gas substantially above atmospheric pressure that reacts with the components within the reaction wells.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE INVENTION

Figure 1:
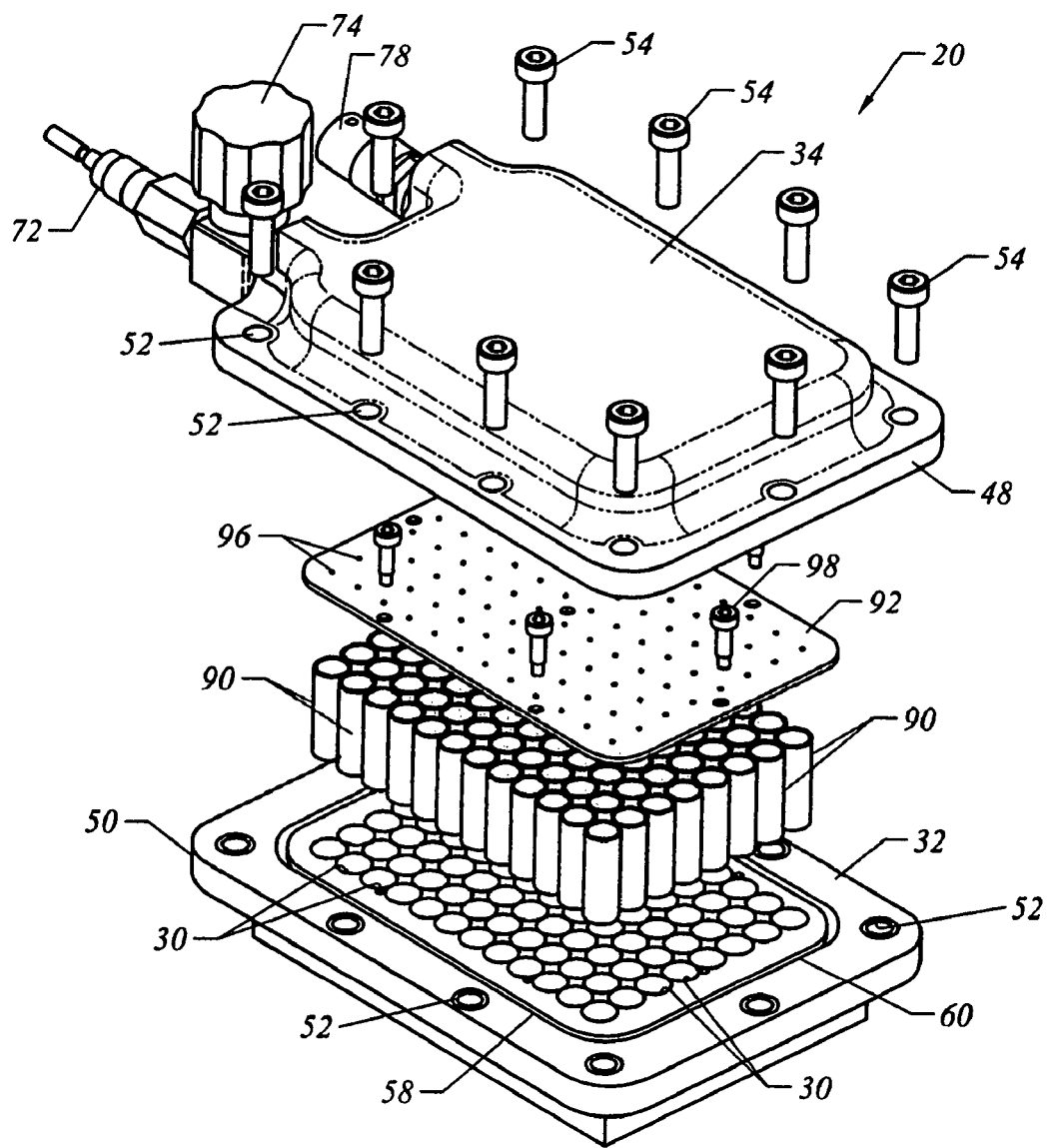
FIG. 1 is an exploded view of a reactor vessel of the present invention.

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Referring now to the drawings, and first to FIGS. 1-6, an apparatus of the present invention is shown and generally indicated at 20. The apparatus 20 comprises a reactor vessel defining a pressure chamber 26 and a plurality of reaction wells 30 internal to the reactor vessel and exposed to the pressure chamber. The pressure chamber 26 is pressurized with an inert gas to pressurize components within the reaction wells or a gas selected to react with components within the reaction wells. The common pressurization area defined by the pressure chamber 26 simplifies the sealing required as compared to individually sealed reaction wells of conventional devices. Furthermore, the common pressure chamber 26 exposes each reaction well 30 to generally the same pressure, whereas individually pressurized reaction wells are often exposed to varying pressures due to leaks or uneven filling (when heated), which introduces undesirable variability into the testing.

The apparatus 20 may be used to perform parallel synthesis or screening of materials or other experimentation involving reactions of multiple components. For example, the apparatus 20 may be utilized for reactions where one or more components is a gas such as hydrogenations, carbonilations, oxidations and polymerizations with gaseous monomers. The apparatus may also be used with homogeneous, chiral, or heterogeneous catalysts (i.e., catalysts which enable catalytic reactions to occur with the reactants and catalysts residing in different phases (e.g., solid/liquid, solid/gas, liquid/gas)), or polyolefin and butyl rubber polymerizations. It is to be understood that the applications described herein are merely examples of uses of the apparatus 20 and methods of the present invention and that the apparatus may be used for other applications without departing from the scope of the invention.

Figure 2:
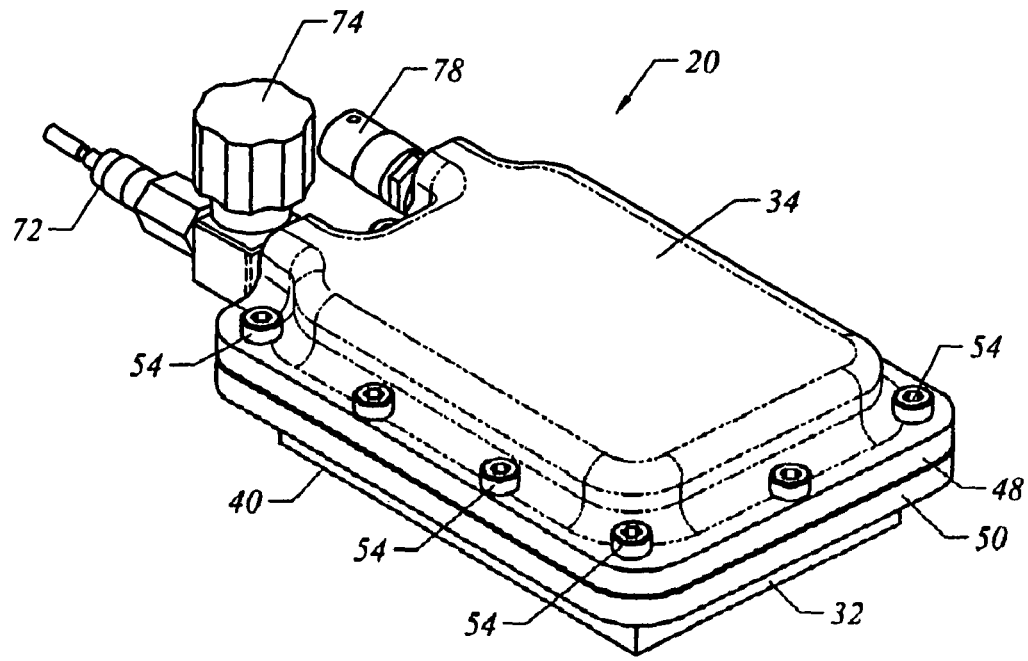
FIG. 2 is a perspective of the reactor vessel of FIG. 1.
Figure 3:
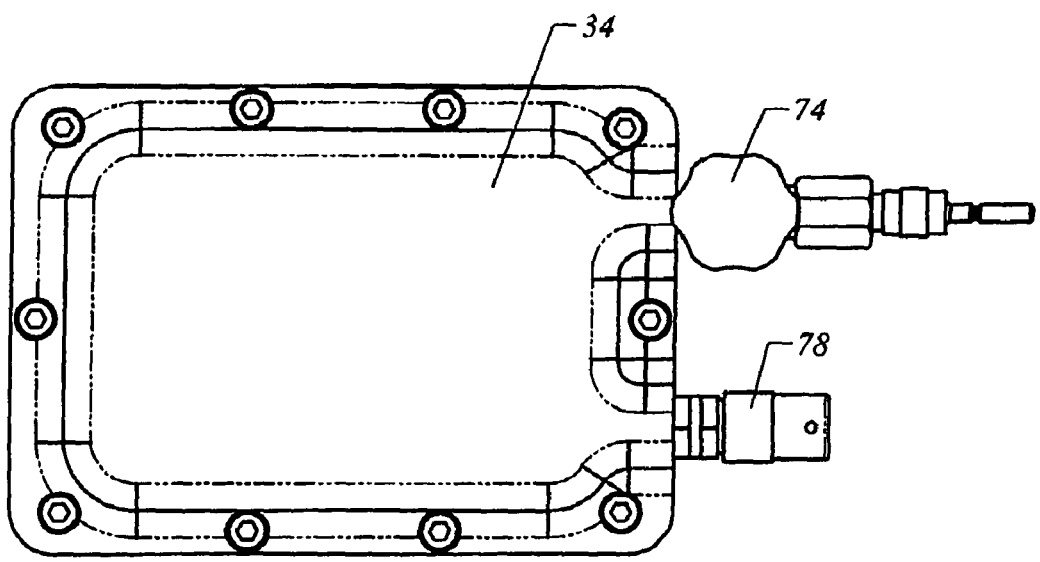
FIG. 3 is a plan view of the reactor vessel of FIG. 1
Figure 4:
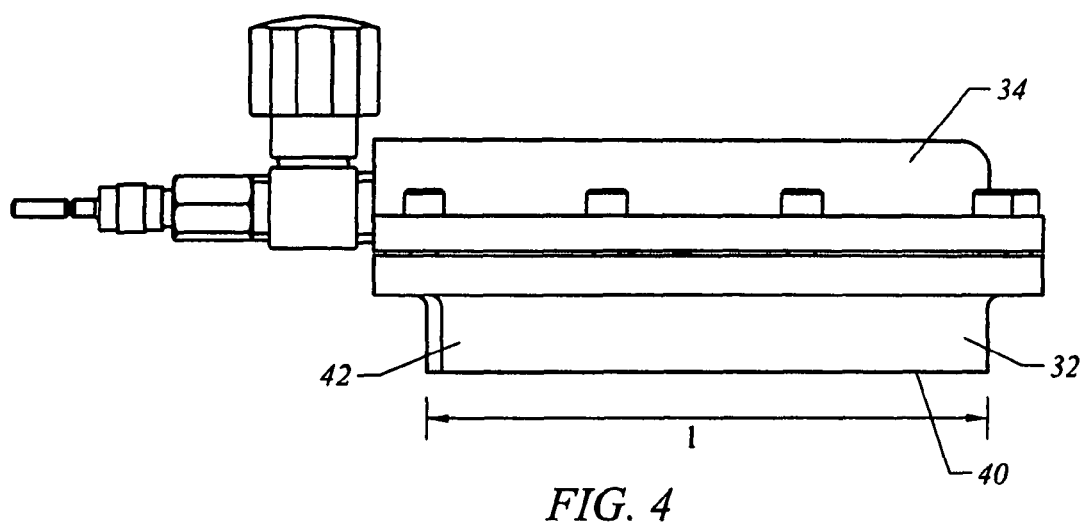
FIG. 4 is a side view of the reactor vessel of FIG. 1.
Figure 5:
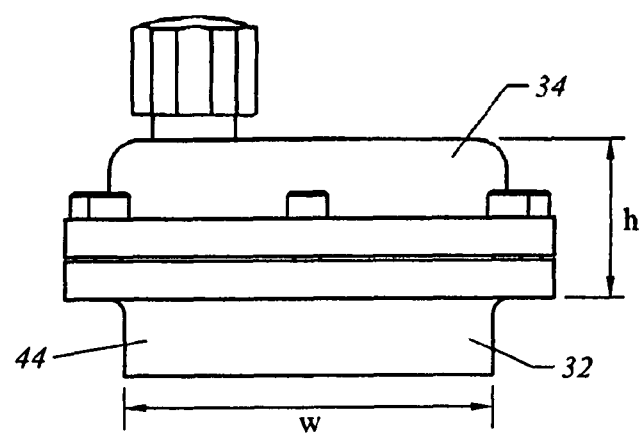
FIG. 5 is a front view of the reactor vessel of FIG. 1.
Figure 7:
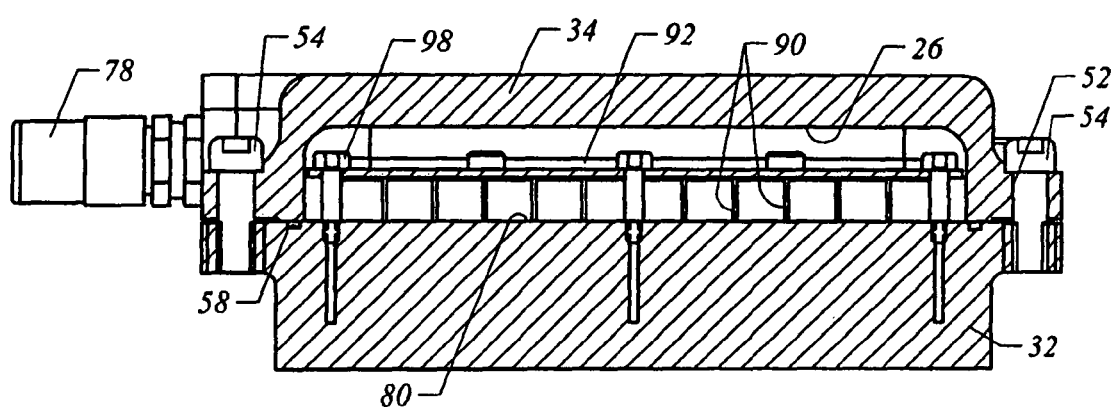
FIG. 7 is a cross-sectional view of the vessel taken in the plane including line 7-7 of FIG. 6.
Figure 8:
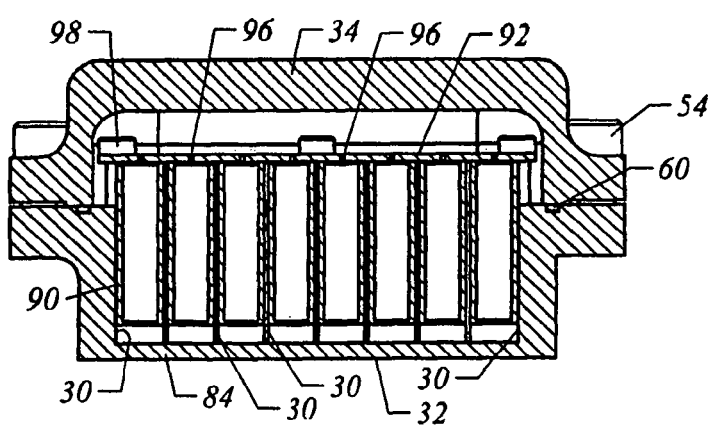
FIG. 8 is a cross-sectional view of the vessel taken in the plane including line 8-8 of FIG. 6.

As shown in FIGS. 1-3, the reactor vessel has an overall rectangular shape and comprises two sections; a base member 32 and a top member (or cover) 34 (FIGS. 1 and 2). The combination of the base 32 and cover 34 form a manifold generally in the form of a rectangular parallelepiped. Internal surfaces of the base 32 and cover 34 define an internal cavity which forms the pressure chamber 26 (FIGS. 7 and 8). The pressure chamber may have a volume of approximately ten cubic inches, for example. The base member 32 includes a bottom 40, a pair of opposing side walls 42, and a pair of opposing end walls 44 (FIGS. 4 and 5). The cover 34 includes a periphery flange 48 configured to mate with a periphery flange 50 extending from the walls 42, 44 of the base member 32 (FIGS. 1 and 2). The flanges 48, 50 of the cover 34 and base 32 include a plurality of openings 52 (ten shown) for receiving bolts 54, screws, or other fasteners. The base 32 and cover 34 may also be attached by other suitable attachment means such as external clamps. The base 32 includes a groove 58 extending around a periphery thereof for receiving a sealing gasket 60 (FIGS. 1, 7 and 8). The gasket 60 is interposed between the base 32 and cover 34 to provide a seal therebetween. The groove 58 for the gasket 60 may be machined into either a bottom surface of flange 48 of the cover 34, or a top surface of flange 50 of the base 32. The gasket 60 may be an o-ring formed from PTFE, neoprene, butyl rubber, Teflon coated elastomer, Viton, expanded Teflon, graphite, or Kalrez, for example.

Figure 6:
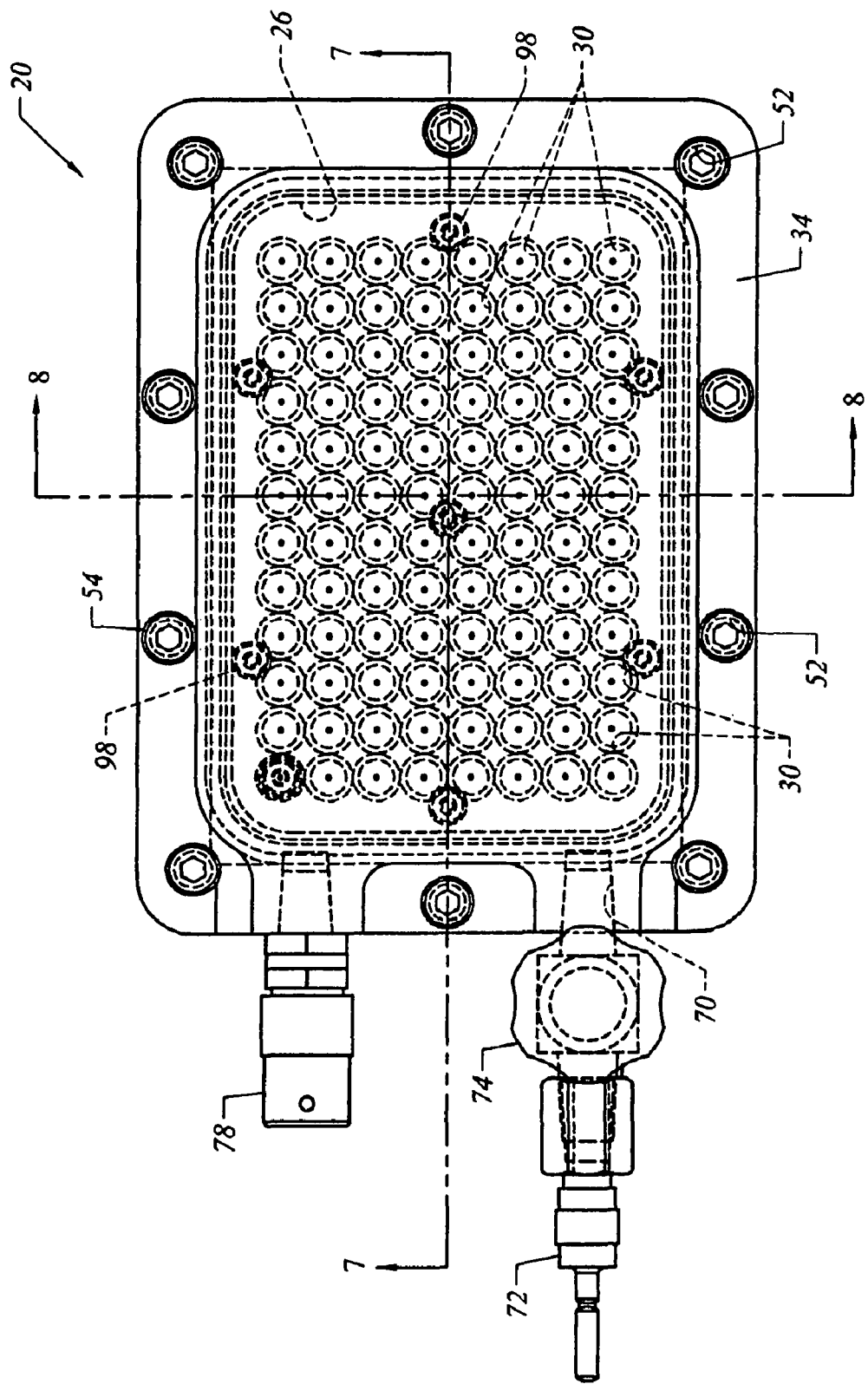
FIG. 6 is a plan view of the reactor vessel of FIG. 1 with internal parts of the vessel shown in phantom.

The reactor vessel includes an inlet port 70 in fluid communication with the pressure chamber 26 (FIGS. 2 and 6). A quick release fitting 72 is preferably coupled to the inlet port 70 for attaching the port to a flexible hose or rigid tube (not shown) connected to a pressure supply device. The flexible hose or rigid gas supply tube may also be left connected and the fill valve open during an experiment. If a vacuum is to be applied to the chamber 26, a vacuum supply device may also be attached to the pressure port 70 or another inlet port on the reactor vessel. A fill valve 74 is attached to the inlet port to control the application of pressure to the vessel. The fill valve 74 may have a manual or electronic pressure control valve. A pressure sensor (not shown) may be inserted inline with the fill valve 74 or inserted into the pressure chamber 26 or one or more of the reaction wells 30 to monitor the pressure within the vessel. The inlet supply system may allow for a series of purging, venting, or pressurization cycles, with one or more gases or with vacuum without disconnecting the supply lines. The pressure source may be an inert gas such as nitrogen, argon, helium, carbon dioxide, or air, or a reactive gas such as hydrogen, oxygen, hydrogen chloride, or ammonia. Mixtures of gases may also be used. The reactor vessel further includes an opening for a pressure release valve 78 to prevent over pressurization of the vessel.

The base 32 and cover 34 may be formed from aluminum, titanium, steel, or any other suitable material. The material of the reactor vessel is preferably selected to be chemically inert to the reaction of interest and allow the vessel to operate at high temperature (e.g., 150-250° C.) and high pressure (10-1000 psig). For example, if the apparatus is to be operated at 290 psig and 150° C. (for e.g., gaseous monomer or reagent use), 6061-T6 aluminum, which has been hard anodized, may be used. If the operating pressure is 1000 psig and operating temperature is 200° C., the material may be 17-4 PH, H1100 stainless steel or 6Al-4V titanium. For some applications, the stainless steel or other material may be coated or surface treated. It is to be understood that the temperature or pressure applied to the reactor vessel or the materials used to form the base 32 and cover 34 may be different than described herein without departing from the scope of the invention. The reactor vessel is preferably designed to withstand pressures substantially above atmospheric pressure (i.e., 14.7 psi). The vessel is preferably designed to withstand pressures above 10 psig, and more preferably pressures above 50 psig. The vessel may also be designed, for example, to operate at pressures of 15 psig, 20 psig, 30 psig, 40 psig, 100 psig, 300 psig, 500 psig, 1000 psig, or other selected pressures. The vessel is preferably designed to withstand temperatures up to 200° C., but may also be designed to operate at 250° C., 315° C., or higher temperatures.

The reaction wells 30 are preferably integrally formed within the base member 32 or another member coupled to the base member. As shown in FIGS. 7 and 8, the wells 30 are machined into an upper planar surface 80 of the base member 32. The wells 30 are preferably machined as close as possible to one another. Similarly, a bottom surface 84 of the well 30 is left with sufficient material to withstand pressures applied to the wells. The base member 32 may also serve as a temperature control means for controlling the reaction temperature in the reaction wells 30, in which case the bottom surface 84 of the reaction wells 30 is sized to provide the required conductivity between an external heat source, such as a heating plate on which the reaction vessel is placed, and the reaction wells. The reactor vessel may be placed, for example, on a temperature control plate which is contiguous to the lower surface of the reactor vessel for the transfer of thermal energy therebetween. The thermal control plate may be a plate formed of thermally conductive material with passages for conveying a heating or cooling fluid through the plate, or other heat generating device, as is well known by those skilled in the art. If the reactor vessel is designed for heating components within the reaction wells, the manifold is preferably formed from a thermally conductive material, such as an aluminum alloy. The reactor vessel may also be placed in an oven to heat the components within the reaction wells 30.

The reaction wells 30 may also be formed within a block separate from the base of the reactor vessel. For example, the reaction wells may be formed within a metal, nylon, Teflon, or other polymer material block. The block may be a microtiter plate, as described below.

The reaction vessel is preferably configured to correspond to a standard microtiter plate format. The microtiter plate is a widely used means for handling, processing, and analyzing large numbers of small samples in the biochemistry and biotechnology fields. Typically, a microtiter plate is approximately 3.4 inches wide and 5.0 inches long and contains 96 identical sample wells in an 8 by 12 rectangular array on 9 millimeter centers. A wide variety of equipment is available for automatic handling, processing, and analyzing of samples in this microtiter plate format. It is to be understood that depending upon the scale of the apparatus, the block may contain a greater or fewer number of reaction wells of various geometries arranged in any configuration.

In the embodiment shown in FIGS. 1-8, the base includes 96 reaction wells 30 in an 8 by 12 array, corresponding to the standard microtiter plate format used in industry for high throughput screening of compounds and biological assays. In preferred embodiments, the number of test wells is equal to 96×N, where N is an integer ranging from 1-100, preferably 1-10, and more preferably 1-5. The outside dimensions of the vessel preferably correspond to the standard microtiter format (e.g., approximately 5.0 inches long (l), 3.4 inches wide (w), and 0.5-2.0 inches high (h) (FIGS. 4 and 5). For example, the reactor vessel may have a length (l) of 5.030 inches, a width (w) of 3.365 inches and height (h) of 2.175 inches. It is to be understood that the reactor vessel may have external dimensions different than the standard microtiter plate format or have a different number or arrangement of reaction wells 30 without departing from the scope of the invention. For example, the reactor may have a 3 by 4 array of reaction wells, each well having a fluid volume of approximately 16 milliliters. Other arrays, such as a 3 by 5 array or a 100 by 100 array may also be used.

Components used in the synthesis or screening may be added directly to the reaction wells 30 or the reaction wells 30 may be lined with an inert liner to prevent reactions between chemicals and the base member. As shown in FIGS. 7 and 8, vials 90 may be inserted into the wells 30 for receiving the components. The vials 90 may be formed from glass or other suitable materials. The vials 90 preferably extend above the reaction well openings formed in the base member 32. The glass vials 90 may have an internal volume of approximately 2 milliliters, for example.

Figure 14:
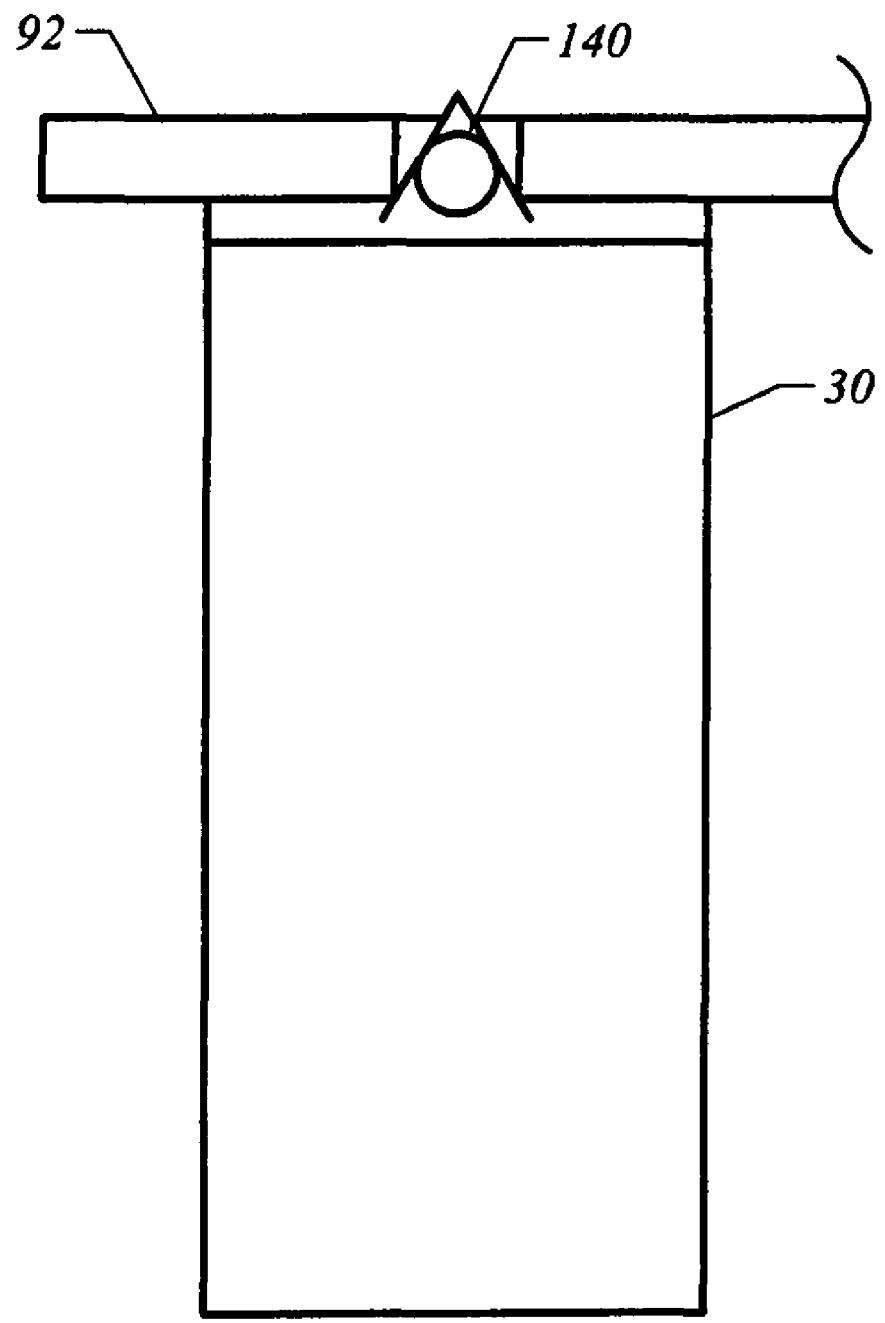
FIG. 14 is a partial cross-sectional view of the vessel of FIG. 1 with a check valve inserted as a flow restriction device.

A flow restriction device 92 is preferably placed over the reaction wells 30 to reduce vapor phase cross-talk between adjacent wells 30 (FIGS. 7 and 8). The flow restriction device 92 may comprise, for example, a cover member having a plurality of very small vent holes 96 aligned with the reaction wells 30 to provide fluid communication between the wells and the pressure chamber 26. The cover member 92 may be a rigid metal plate with vent holes drilled therein or a flexible elastomeric sheet (e.g., septum sheet) with vent holes punched therein. The member 92 may also be a porous sheet with the pores providing fluid communication between the reaction wells 30 and the pressure chamber 26. The flow restriction device 92 may also include check valves 140 which allow flow into the reaction wells 30 but restrict flow from the reaction wells to the pressure chamber 26 (shown schematically in FIG. 14). The vent holes within the flow restriction device 92 may also be micromachined flow restrictions.

Figure 9:
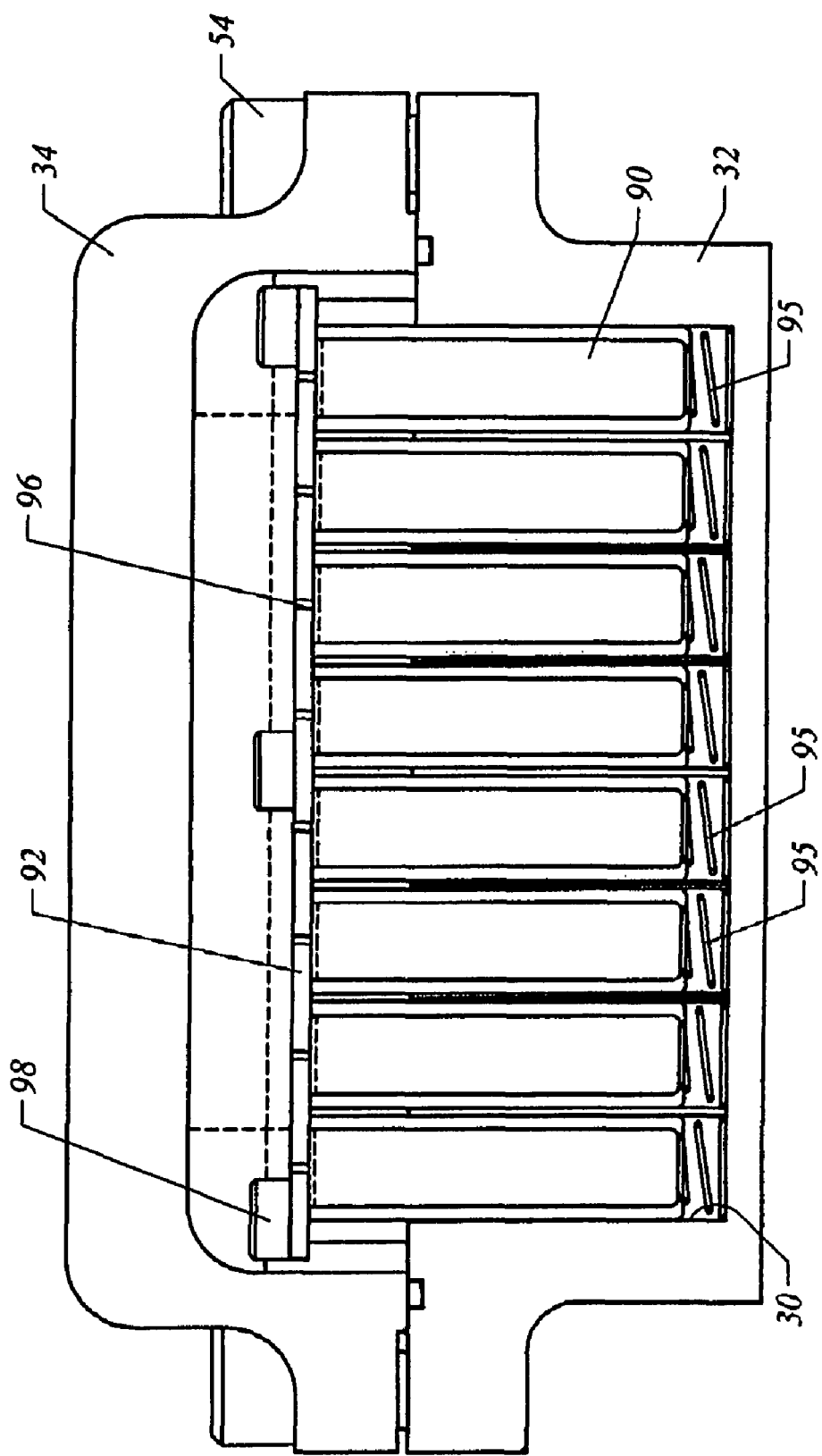
FIG. 9 is a cross-sectional view of the vessel taken in the plane including line 8-8 of FIG. 6 with coil springs disposed at a closed bottom of reaction wells to force vials within the wells upward against a cover plate.

A coil spring 95 (or elastomeric material) may be placed at the bottom of each of the reaction wells to force the vials upward and bias the open ends of the vials against the flow restriction device 92, as shown in FIG. 9. The flow restriction device 92 is preferably removably attached to the base member with bolts 98 or other suitable attachment means. The flow restriction device 92 may also be coupled or integrally formed with the cover 34 so that the device is automatically disposed adjacent to the open ends of the reaction wells 30 when the cover is mated with the base member 32 and closed.

The materials of the base member 32, cover 34, flow restriction device 92, gasket 60, and vials 90 are preferably selected to be chemically suitable for the application (i.e., will not be attacked, solubilized, softened, or otherwise interact with the reagents, solvents, solids, products, or other components which are either added to the vessel or produced during a reaction sequence). The materials are also preferably chosen to assure that reactant, products, or by-products of the reaction are not adsorbed or otherwise trapped by the materials.

Figure 10:
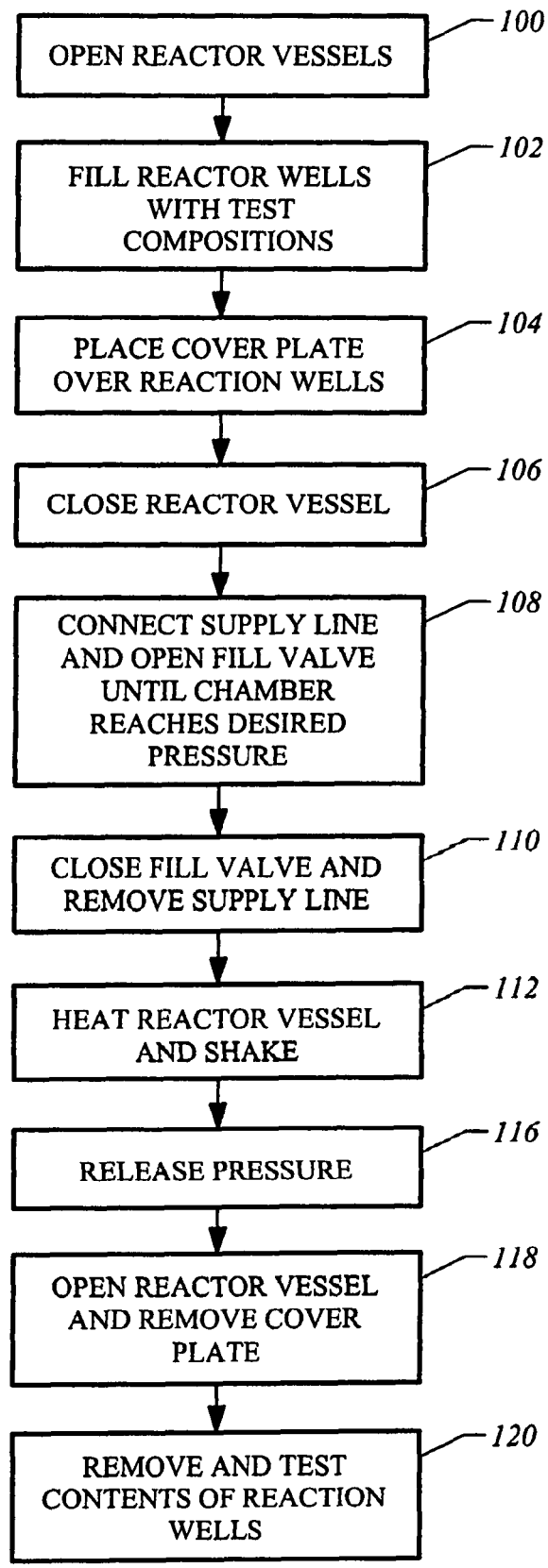
FIG. 10 is a flowchart illustrating a process utilizing the reactor vessel of FIG. 1.

FIG. 10 is a flowchart illustrating a process for utilizing the apparatus 20 of the present invention. At step 100, the cover 34 is removed from the base member 32 (or placed in an open position) to allow access to the interior of the reactor vessel (FIGS. 1 and 10). If the reaction wells are not formed in the base member, the block containing the reaction wells is positioned within the base member 32. The components to be tested are then placed within the reaction wells 30 (step 102). Preferably, the composition of the materials placed within each of the wells 30 varies from one reaction well to the next. The cover plate 92 is then placed over the base member 32 with fastener openings within the plate aligned with openings formed in the base (or reaction well block) (step 104). Bolts 98 or other suitable fasteners, are inserted into the aligned openings to attach the cover plate 92 to the base member 32. The cover 34 is then attached to the base 32 with bolts 54 or other fasteners (step 106). A supply line (not shown) is connected to the quick release coupling 72 at the inlet port 70 and the fill valve 74 is opened until the required pressure is reached within the pressure chamber 26 (step 108) (FIGS. 6 and 10). The gas supplied to the vessel may be an inert gas or a gas that reacts with the components placed into the reaction wells 30.

After the pressurized gas is added to the vessel and the pressure chamber 26 has reached the appropriate operating pressure, the fill valve 74 is closed, the supply line is removed, and the entire assembly is inserted into an oven or placed on a heating plate (steps 110 and 112). Agitation of components within the reaction wells 30 may be achieved by shaking or magnetic stirring. For example, the apparatus may be placed on an oven/shaker assembly or a magnetic stirrer may be used to mix the reactants. The base 32 and cover 34 are preferably aluminum or titanium if magnetic stirring is used. Once the reaction is complete, pressure is removed from the pressure chamber 26 through the fill valve 74 or an outlet or vent within the housing (step 116). The cover 34 is opened and the cover plate 92 is removed from the base member 32 (step 118). If vials 90 are used, the vials are removed from the reaction wells 30 for analysis or their contents are sampled (step 120). If the materials are placed directly into the reaction wells 30, a pipette or other suitable tool may be used to remove contents of the wells. The contents of the reaction wells 30 are then analyzed by techniques well known by those skilled in the art.

Figure 11:
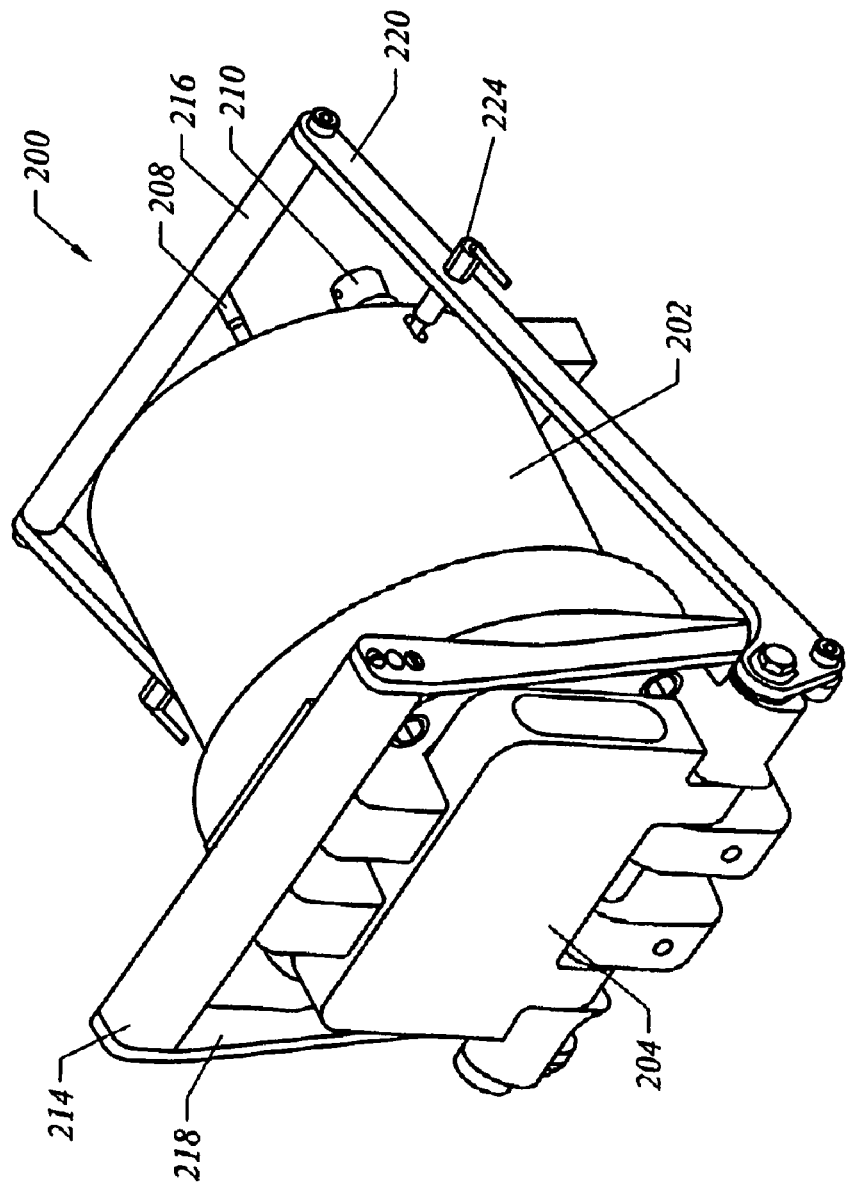
FIG. 11 is a perspective of a second embodiment of a reactor vessel of the present invention.
Figure 12:
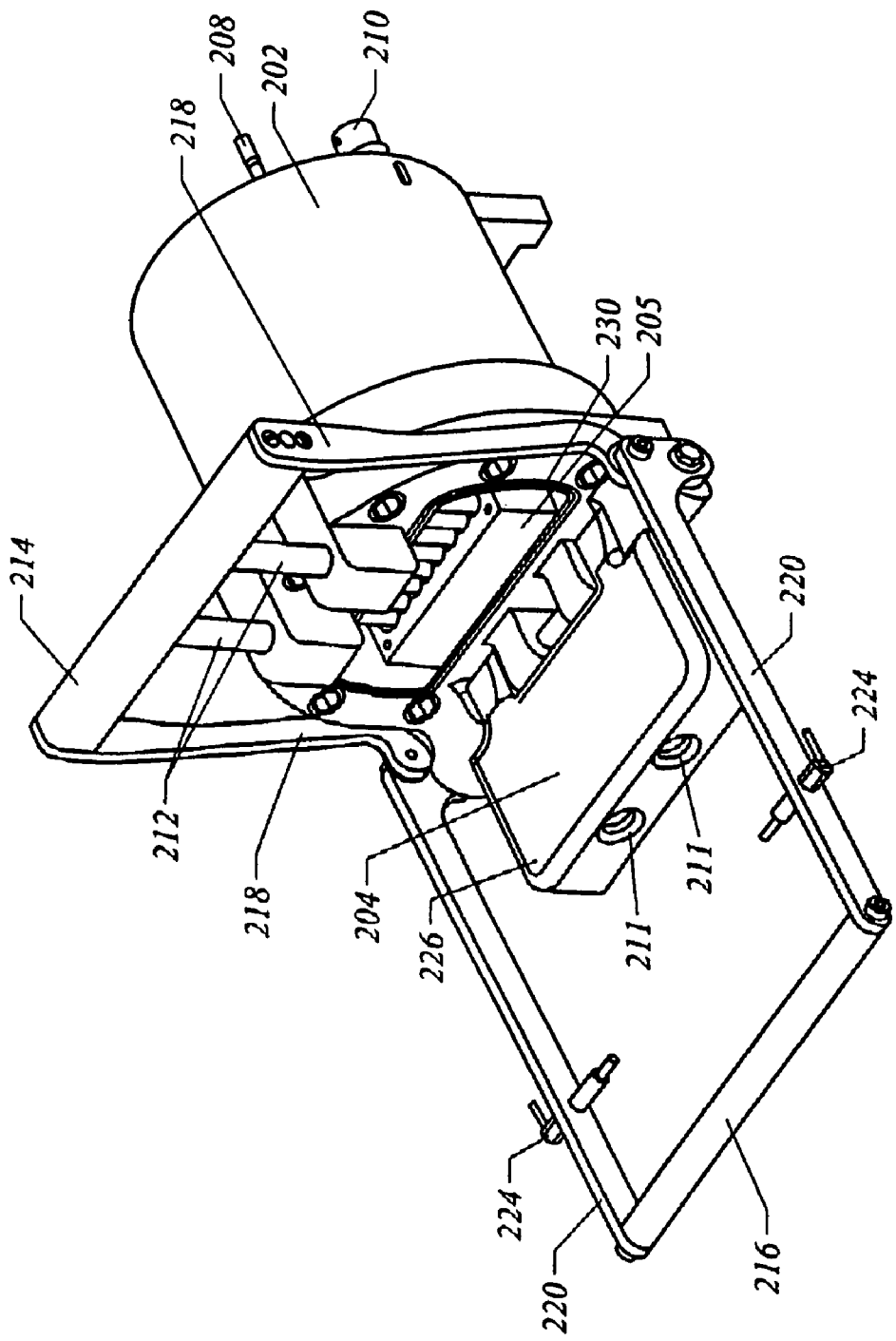
FIG. 12 is a perspective of the reactor vessel of FIG. 11 in an open position.
Figure 13:
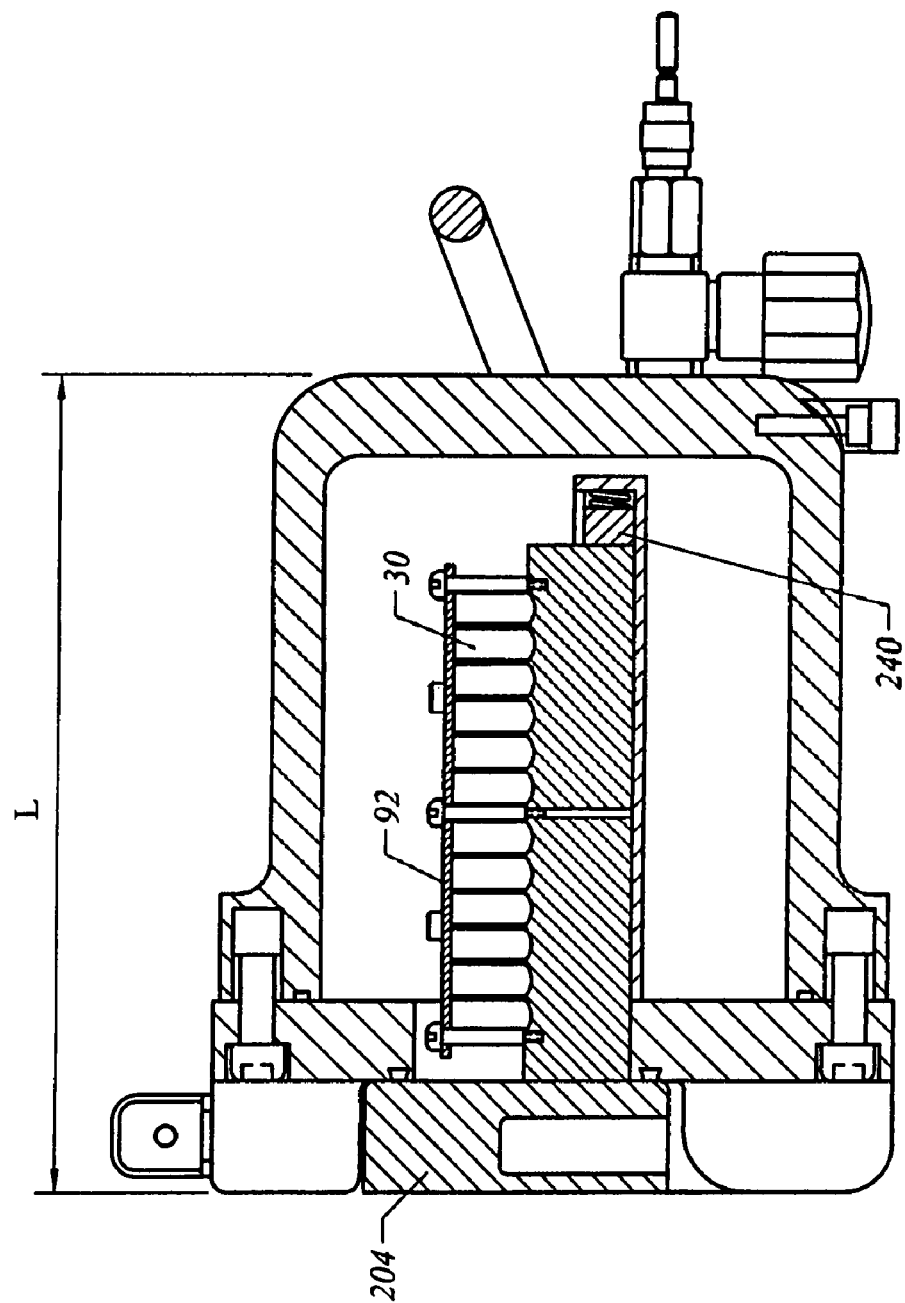
FIG. 13 is a cross-sectional view of the reactor vessel of FIG. 11.

FIGS. 11-13 show a second embodiment of a reactor vessel of the present invention, generally indicated at 200. The reactor vessel 200 includes a pressure chamber 202 sized for receiving a microtiter plate 205. The pressure chamber 202 may be formed from 6061-T6 aluminum, or any other suitable material. The vessel 200 includes a fill valve 208 and pressure relief valve 210 in communication with the pressure chamber 202. The vessel 200 further includes a door 204 movable between an open position (shown in FIG. 12) for inserting the microtiter plate 205 and a closed position (shown in FIG. 11) for creating a sealed pressure chamber. A quick-operating fastening device is used to move the door 204 to its closed position and sealingly engage the door with the pressure chamber 202. The door 204 may be formed from stainless steel or other suitable materials. The door 204 includes two pin receiving openings 211 formed in a top surface of the door and extending longitudinally through a portion of the door (FIG. 12). The openings 211 are sized for receiving door latching pins 212 which extend downwardly from latch mechanism 214. The latch mechanism 214 is coupled to a handle 216 for movement therewith. The latch mechanism 214 and handle 216 each include a pair of legs 218, 220, respectively. The legs 218 of the latch mechanism 214 are spaced apart such that each leg is positioned adjacent to an inner surface of the legs 220 of the handle 216. The legs 218, 220 are attached by bolts or other suitable attachment means to create a four bar mechanism. The door 204 may also be coupled to the handle 216 so that the door rotates towards its closed position as the handle is rotated upwardly.

When the handle 216 is in its open position the latching mechanism 214 is in a raised positioned (FIG. 12). As the handle 216 is rotated upwardly it pulls the door latching mechanism 214 downwardly along a linear axis and forces the pins 212 into the pin receiving openings 211 within the door 204 as the door is rotated upwardly by the handle (FIG. 11). The handle 216 includes latching members 224 attached to the legs 220 thereof to lock the door 204 in its closed position. When the door 204 is in its closed position, an inner surface 226 of the door is in sealing engagement with and an o-ring 230 positioned within a groove extending around the periphery of the opening in the pressure chamber 202. A spring loaded clamping device 240 is positioned adjacent to the end of the plate 205 opposite the door 204 to hold the plate in place. The quick-operating fastening device allows for quick and easy opening and closing of the vessel without the need to loosen or tighten bolts or other attachment means.

The entire assembly 200 may be placed into an oven or on an orbital shaker. As shown and described above, the vessel 200 is compact since it is sized specifically for receiving a microtiter plate. For example, the vessel 200 may have a length (L) of 7.625 inches. It is to be understood that the vessel may have different configurations than shown and described herein without departing from the scope of the invention. For example, the vessel 200 may be sized for receiving more than one microtiter plate or have a quick release mechanism different than shown.

The following examples illustrate principles and advantages of the invention.

EXAMPLE 1

Heterogeneous Catalysis

The reaction vessel used for this experiment was formed from 6061-T6 aluminum and had 96 reaction wells. The following components were first added to a 4 ml glass vial to form a solution:
  10.9 mg of 1% palladium on activated carbon;
  3.090 ml ethyl alcohol; and
  0.020 ml nitrobenzene.

The vial was shaken by hand and then placed on a stir plate to mix using a magnetic micro-stir bar within the vial. Samples containing 0.377 ml of the solution were pipetted into two of the 96 wells. The reactor was then sealed with an o-ring and the cover was placed over the base of the reactor. Bolts were inserted into the aligned openings of the base and cover and each torqued to 10 ft-lbs. A gas supply line was attached to the reactor vessel and the vessel was pressurized and vented three times to remove the air inside. The vessel was then pressurized to 30 psig with pure hydrogen gas. The fill valve was closed and the gas line disconnected before placing the apparatus in a mixing oven. The reactor was heated at 30° C. for one hour while mixing. The vessel was then vented and opened. Thin layer chromatography (TLC) and high pressure liquid chromatography (HPLC) were performed and showed that the nitrobenzene in both wells was fully converted and only the desired product, aniline, was detected.

EXAMPLE 2

Cross-Talk

In the following example, two aluminum reactor vessels each having 96 reaction wells were used. One of the reactor vessels included a septum sheet (flow restriction device) having punctured holes aligned with each of the reaction wells. The other reactor vessel did not include a flow restriction device to reduce cross talk between reaction wells. Blanks of pure toluene were placed in eight reaction wells within each of the reactors. The remaining reaction wells contained a mixture of heptane, toluene, and octene. Nitrogen gas was supplied to each of the reactor vessels at an initial pressure of 160 psig and temperature of 25° C. The final pressure within the vessels was 260 psig after 45 minutes in an oven at 200° C. The following are the gas chromatography (GC) test results:

The original mix before the test included the following components:
  43.47% heptane, 49.03% toluene, and 7.50% octene.

The original toluene blank before the test contained:
  0.05% (in heptane position), 99.93% toluene, and 0.02% (in octene position).

The average composition of the mix (with flow restriction device) after the test was:
  41.51% heptane, 51.35% toluene, and 7.14% octene.

The average composition of the mix (without flow restriction device) after the test was:
  41.82% heptane, 50.50% toluene, and 7.68% octene.

Thus, some vapor was being transported out of the reaction wells in both reactor vessels.

The average composition of the toluene blanks (with flow restriction device) after the test was:
  0.47% heptane, 99.49% toluene, and 0.04% octene.

The average composition of the toluene blanks (without flow restriction device) after the test was:
  17.11% heptane, 81.26% toluene, and 1.68% octene.

Thus, the flow restriction device helped to prevent vapor transport (cross-talk) into the wells.

As can be observed from the foregoing, the apparatus 20, 200 and method of the present invention have numerous advantages. The reaction wells 30 are all exposed to a common pressure chamber 26 which results in simplification of the apparatus, reduced variation between pressurization of the reaction wells, and reduced manufacturing and processing costs. The apparatus is well suited for auxiliary processes including heating, shaking, and robotic automation. Furthermore, since there is a fewer number of sealed volumes (e.g., one versus ninety-six) the apparatus provides increased reliability and easier maintenance. The design of the reactor vessel allows for pressurization of the reaction wells with a pressurized gas at a pressure substantially above atmospheric pressure.

Although the present invention has been described in accordance with the embodiments shown, one of ordinary skill in the art will readily recognize that there could be variations made to the embodiments without departing from the scope of the present invention. Accordingly, it is intended that all matter contained in the above description and shown in the accompanying drawings shall be interpreted as illustrative and not in a limiting sense.

What is claimed is:

1. A parallel batch reactor comprising:
a base having a plurality of reaction wells formed therein, each of said reaction wells having a closed lower end and an open upper end for receiving components for the reaction;
a cover configured for sealing engagement with the base to form a housing enclosing said plurality of reaction wells and defining a common pressure chamber in communication with said plurality of reaction wells;
an inlet port in communication with said pressure chamber for supplying pressurized fluid to said chamber to pressurize said plurality of reaction wells; and
a plurality of check valves positioned between said plurality of reaction wells and said pressure chamber and configured to allow flow into said plurality of reaction wells and restrict flow from said plurality of reaction wells to provide communication between said plurality of reaction wells and said pressure chamber while reducing cross-talk between two or more of said plurality of reaction wells;
wherein the material and structure of the pressure chamber is such that the chamber is operable to sustain an operating pressure above 40 psig.

2. The parallel batch reactor of claim 1 wherein the housing is configured to sustain an operating pressure equal to or greater than 300 psig.

3. The parallel batch reactor of claim 1 wherein the housing is configured to sustain an operating pressure equal to or greater than 1000 psig.

4. The parallel batch reactor of claim 1 wherein the base and cover are formed from titanium.

5. The parallel batch reactor of claim 1 wherein the base and cover are formed from aluminum.

6. The parallel batch reactor of claim 1 wherein the base and cover are formed from stainless steel.

7. The parallel batch reactor of claim 1 further comprising a quick release fitting coupled to the inlet port for connecting the inlet port to a pressure source.

8. The parallel batch reactor of claim 1 further comprising a pressure relief valve coupled to an outlet port in communication with said common pressure chamber.

9. The parallel batch reactor of claim 1 wherein the cover is removably attached to the base member.

10. The parallel batch reactor of claim 1 wherein external dimensions of the base member and cover generally correspond to standard microtiter plate dimensions for use with automation equipment designed for use with microtiter plates.

11. The parallel batch reactor of claim 10 wherein said plurality of reaction wells comprises 96 reaction wells arranged in an 8 by 12 array.

12. The parallel batch reactor of claim 11 wherein the reaction wells each have an internal volume of approximately 2 milliliters.

13. The parallel batch reactor of claim 1 wherein said plurality of reaction wells comprises 12 reaction wells arranged in a 3 by 4 array.

14. The parallel batch reactor of claim 13 wherein each of said reaction wells has an internal volume of approximately 16 milliliters.

15. The parallel batch reactor of claim 1 wherein said plurality of reaction wells are spaced approximately 9 mm apart center to center.

16. The parallel batch reactor of claim 1 wherein a circumferential groove is formed in one of the base and cover and a gasket is disposed within said groove to provide a seal between the base and the cover.

17. The parallel batch reactor of claim 1 wherein the base and cover each have a periphery flange extending therefrom and configured for mating with the other of the base and cover.

18. The parallel batch reactor of claim 1 further comprising a plurality of vials inserted into said plurality of reaction wells for receiving reaction components.

19. The parallel batch reactor of claim 1 wherein said pressure chamber has a volume of approximately ten cubic inches.

* * * * *